US012733791B2

(12) United States Patent
Schroeter et al.

(10) Patent No.: US 12,733,791 B2
(45) Date of Patent: Sep. 15, 2026

(54) ENDOSCOPE HAVING A NOZZLE ELEMENT FOR CLEANING A LENS ELEMENT

(71) Applicant: HOYA CORPORATION, Tokyo (JP)

(72) Inventors: Tilman Schroeter, Friedberg (DE); Stefan Kolberg, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 365 days.

(21) Appl. No.: 18/266,451

(22) PCT Filed: Jun. 9, 2022

(86) PCT No.: PCT/EP2022/065723
§ 371 (c)(1),
(2) Date: Jun. 9, 2023

(87) PCT Pub. No.: WO2022/258765
PCT Pub. Date: Dec. 15, 2022

(65) Prior Publication Data
US 2024/0090745 A1 Mar. 21, 2024

(30) Foreign Application Priority Data
Jun. 10, 2021 (DE) ........................ 102021114984.3

(51) Int. Cl.
*A61B 1/00* (2006.01)
*A61B 1/12* (2006.01)

(52) U.S. Cl.
CPC ...... *A61B 1/00091* (2013.01); *A61B 1/00096* (2013.01); *A61B 1/126* (2013.01)

(58) Field of Classification Search
CPC .. A61B 1/00091; A61B 1/00096; A61B 1/126
See application file for complete search history.

(56) References Cited

U.S. PATENT DOCUMENTS 6,142,932 A * 11/2000 Morizumi .......... A61B 1/00193 600/176
8,591,406 B2 11/2013 Hirayama
(Continued)

FOREIGN PATENT DOCUMENTS

CN 103813744 A 5/2014
EP 2859835 A1 * 4/2015 ......... A61B 1/00091
(Continued)

OTHER PUBLICATIONS

International Search Report issued in International Bureau of WIPO Patent Application No. PCT/EP2022/065723, dated Sep. 28, 2022.
(Continued)

*Primary Examiner* — Michael J Carey
*Assistant Examiner* — Stephen Floyd London
(74) *Attorney, Agent, or Firm* — Greenblum & Bernstein, P.L.C.

(57) ABSTRACT

An endoscope with a distal housing element which has a lens element, and with a nozzle element for cleaning the surface of the lens element. The lens element is a curved lens element, the curvature of which protrudes from the housing element in a distal direction. The nozzle element is arranged at the distal side of the distal housing element adjacent to the curved lens element. The nozzle element has a distal nozzle opening in the form of an elongated medium outlet slit directed toward the curved lens element.

17 Claims, 13 Drawing Sheets

(56) References Cited

U.S. PATENT DOCUMENTS

| | | | | |
|---|---|---|---|---|
| 2011/0112363 | A1* | 5/2011 | Koga | A61B 1/126 600/109 |
| 2012/0226104 | A1* | 9/2012 | Ikeda | A61B 1/126 600/129 |
| 2014/0094659 | A1* | 4/2014 | Hamazaki | G02B 23/2476 600/157 |
| 2016/0309994 | A1* | 10/2016 | Kuwae | A61B 1/12 |
| 2017/0150873 | A1* | 6/2017 | Tatebayashi | A61B 1/05 |
| 2019/0090723 | A1* | 3/2019 | Tanaka | A61B 1/00094 |
| 2019/0090729 | A1 | 3/2019 | Sugiura et al. | |
| 2019/0174999 | A1* | 6/2019 | Wake | A61B 1/00089 |
| 2020/0000320 | A1 | 1/2020 | Tajima et al. | |
| 2021/0177249 | A1 | 6/2021 | Watanabe | |
| 2022/0330802 | A1 | 10/2022 | Watanabe | |
| 2022/0409034 | A1* | 12/2022 | Takasaki | A61B 1/126 |

FOREIGN PATENT DOCUMENTS

| | | | | |
|---|---|---|---|---|
| EP | 2886037 | A1 * | 6/2015 | A61B 1/00091 |
| JP | 2020-156902 | A | 10/2020 | |

OTHER PUBLICATIONS

First Office Action issued in Chinese patent application No. 202280007827.8, dated Feb. 2, 2026, together with an English translation.

* cited by examiner

ENDOSCOPE HAVING A NOZZLE ELEMENT FOR CLEANING A LENS ELEMENT

The invention relates to an endoscope with a nozzle element for cleaning a lens element. More specifically, the invention relates to an endoscope with a distal housing element which has a lens element, and a nozzle element for cleaning the surface of the lens element.

An endoscope is inserted into a patient for the purpose of an examination or a surgical intervention. At the target of the examination or when the endoscope is being moved to the target, the environment of the endoscope can be illuminated by emission of light from the endoscope. The illuminated environment can be viewed by means of a camera. The light captured by the camera is incident via a lens element arranged at a housing element of the endoscope. To keep the lens element free of contamination, it is cleaned also during use by a nozzle element releasing a cleaning medium for cleaning the surface of the lens element.

It is an object of the invention to provide an improved endoscope with a nozzle element for cleaning a lens element that satisfies high demands and in which the lens element can be optimally cleaned.

This object is achieved by means of an endoscope having the features of Claim 1. Advantageous further examples are subject of the dependent claims.

The invention relates to an endoscope with a distal housing element that has a lens element, and with a nozzle element for cleaning the surface of the lens element, wherein the lens element is a curved lens element, the curvature of which protrudes from the housing element in a distal direction, the nozzle element is arranged at the distal side of the distal housing element adjacent to the curved lens element, and the nozzle element has a distal nozzle opening in the form of an elongated medium outlet slit directed toward the curved lens element.

In this endoscope, even a curved lens element can be advantageously cleaned by the nozzle element releasing a cleaning medium through the elongated medium outlet slit. By using an elongated medium outlet slit at the nozzle element, the released jet of the cleaning medium is extended already at the nozzle outlet. A laterally expanded flow of the cleaning medium is created, which is directed toward the curved lens element. In this way, a cleaning jet can be directed toward the curved lens element which is already widened laterally when it strikes the curved lens element. The lens element can thus be optimally cleaned.

The elongated medium outlet slit can extend transverse to the extension direction of the endoscope. Such a medium outlet slit provides a laterally expanded cleaning jet that has a large extent transverse to the extension direction of the endoscope. When such a laterally widened cleaning jet strikes a side of the curved lens element facing the nozzle element, a broad region of the curved lens element and the lateral surroundings of the curved lens element may be submerged by the cleaning jet. This means the lens element can be cleaned even better.

The curved lens element can have an area Fu to be flowed over which is formed at least by the entire exposed lens surface, with the distal nozzle opening having a nozzle opening area Fd, where $30<\text{Fü}/\text{Fd}<40$. The exposed lens surface refers to the lens surface that protrudes from the housing element in which the curved lens element is embedded. The inventors of the present invention have discovered that the ratio of $30<\text{Fü}/\text{Fd}<40$ of the area Fu of the lens element to be flowed over to the nozzle opening area Fd of the nozzle element results in a fluid flow that is particularly advantageous for submerging at least the entire exposed lens surface.

The distal nozzle opening can have a smaller width than a width bü of the curved lens element at the proximal edge of the curved lens element. The flow of the fluid released from the nozzle element expands toward the lens element, thus the width of the fluid flow becomes wider and can cover at least the entire exposed lens surface. Since the distal nozzle opening can have a smaller width than the width bü of the curved lens element at the proximal edge of the curved lens element, a narrower nozzle element can be used which does not have to occupy the entire corresponding width bü of the curved lens element at the proximal edge.

The distal nozzle opening can be aligned with respect to the curved lens element such that the flow exiting from the distal nozzle opening is directed approximately tangential with respect to the proximal edge of the curved lens element. This results in an advantageous overflowing over the exposed lens surface. If the fluid flow passes the most distal point of the exposed lens surface (highest point of the exposed lens surface) of the curved lens element, the flow does not break down and continues to move on the exposed lens surface away from the distal nozzle opening. Thus, even the portion of the exposed lens surface located on the far side of the nozzle element can be cleaned well.

The flow exiting from the distal nozzle opening can be directed with respect to the proximal edge of the curved lens element at an angle of $-10^\circ<\text{Ltgü}<+20^\circ$, where Ltgü is the tangent to the lens surface of the curved lens element at the proximal edge of the curved lens element, a positive angle extends away from the curved lens element at the proximal edge of the curved lens element, and a negative angle extends into the curved lens element at the proximal edge of the curved lens element. The inventors of the present invention have found that $-10^\circ<\text{Ltgü}<+20^\circ$ is particularly advantageous for submerging at least the entire exposed lens surface.

The distal nozzle opening can be arranged proximal to the proximal edge of the curved lens element. In this way, the fluid flow is released toward the distal side. The nozzle element does not protrude beyond the curved lens element in the distal direction. The insertion of the endoscope is thus not affected by the nozzle element.

The distal nozzle opening can be arranged spaced apart from the proximal edge of the curved lens element by a distance L, wherein the distance L is less than or equal to half the width bi of the curved lens element at the proximal edge of the curved lens element. At this distance L, an advantageous widening of the released fluid jet is obtained, which on striking the proximal edge of the curved lens element has attained a width (lateral extension) that corresponds to the width of the proximal edge of the curved lens element. After the fluid flow has passed the proximal edge of the curved lens element, it widens further such that at least the entire exposed lens surface is submerged.

The lens element can be a curved lens element, the curvature of which is spherical or aspherical. Irrespective of the shape of the exposed lens surface, the lens element can be advantageously flushed.

The distal nozzle opening can form a single distal opening of the nozzle element. Multiple openings at a nozzle element are not required. Furthermore, multiple nozzle elements are not required. The single distal opening of the nozzle element alone ensures the advantageous cleaning of the curved lens element.

The curved lens element can comprise the area Fu to be flowed over, which is formed by the entire exposed lens surface, and the area Fu to be flowed over can be greater than a quarter of the cross-sectional area Fe of the endoscope at the distal housing element. Even at this size, at least the entire exposed lens surface of the curved lens element can be flowed over. At least the entire exposed lens surface is to be understood as meaning that the fluid flow can also be broader and cover edge portions of the distal side of the distal housing element adjacent to the curved lens element, which abut the curved lens element. In this way, even the edge portions of the exposed lens surface abutting the distal side of the distal housing element are cleaned well.

The distal nozzle opening in the form of an elongated medium outlet slit can have a width bd and a height hd, wherein hd<bd. The distal nozzle opening is thus wider than it is high and has a very small height. In this way, only a small nozzle element is required, which protrudes slightly from the distal side of the distal housing element in order to advantageously clean the curved lens element.

In a further example, the distal nozzle opening in the form of an elongated medium outlet slit can have a width bd and a height hd, wherein hd<1 mm<bd.

The aspects of the present invention explained above can be appropriately combined.

BRIEF DESCRIPTION OF THE DRAWINGS

FIG. 4 shows a schematic perspective view of a distal housing element according to the invention with a lens element and a nozzle element in a second example.

Figure 1:
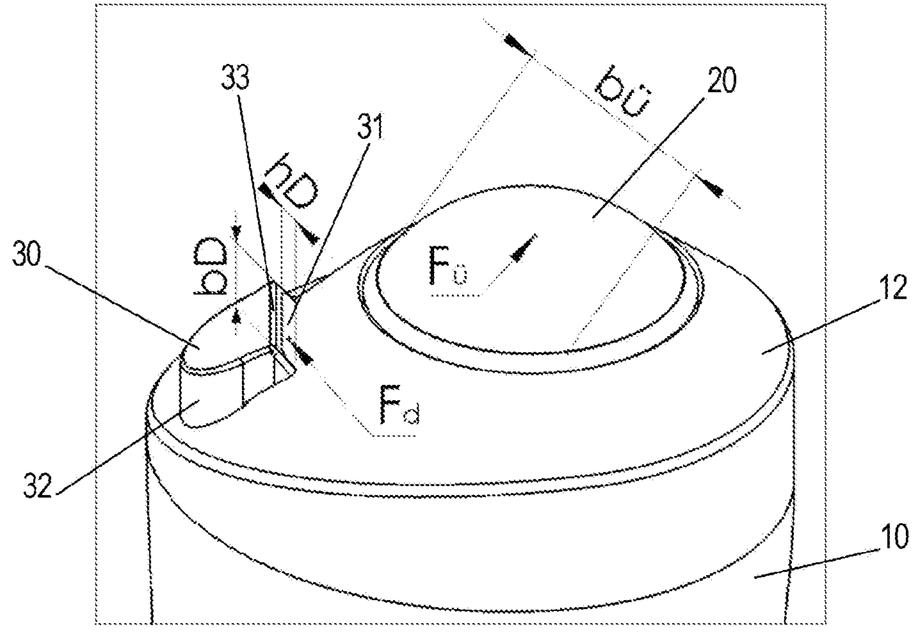
FIG. 1 shows a schematic perspective view of a distal housing element according to the invention with a lens element and a nozzle element in a first example.

The present invention is described in detail below with reference to the drawings and based on examples. The illustrations in the drawings are not necessarily shown to scale but are sometimes shown exaggerated for better clarity.

FIRST EXAMPLE

A first example of the present invention is described below with reference to FIGS. 1 to 3.

An endoscope has a proximal handle body (not shown) at which an insertion tube or insertion body (not shown) extends distally from the handle body. A distal housing element 10 is formed at the distal end of the insertion tube or insertion body.

When inserting the insertion tube or insertion body into a body that is to be examined, the endoscope is inserted with the distal housing element 10 in front. The distal housing element 10 is formed cylinder-like, for example. The distal housing element 10 can be formed as a cylinder with a circular cross-section or an oval cylinder, see FIG. 3.

The distal housing element 10 has a distal side 12, which faces in the distal direction—that is, away from the proximal handle body. Preferably, the distal side 12 of the distal housing element 10 rises in the distal direction from the edge of the distal housing element 10 toward the inner side, see FIGS. 1 and 2.

The distal housing element 10 can accommodate an optical system. The optical system can consist of an image acquisition device (a camera objective) and an illumination device. The illumination device illuminates the scene surrounding the distal housing element 10. An image of this environment can then be acquired by means of the image acquisition device.

In this example, the image acquisition device has a wide-angle lens or fish-eye lens to enable a particularly wide field of view.

A lens element 20 is therefore arranged at the distal housing element 10 at the distal side 12. Preferably, the lens element 20 is arranged at a region of the distal side 12 located furthest away in the distal direction. The lens element 20 is a curved lens element, the curvature of which protrudes from the housing element 10 in a distal direction. In this example, the lens element 20 is a curved lens element with spherical curvature. The lens element 20 is thus such a wide-angle lens or fish-eye lens.

In the example, the lens element 20 is arranged spaced apart from the circumferential edge of the distal housing element 10. In other words, the lens element 20 is arranged at the distal side 12 in such a way that the body of the lens element 20 protruding from the distal side 12 in the distal direction is always spaced apart from the circumferential edge of the distal housing element 10 extended in the distal direction.

The lens surface of the lens element 20 can become contaminated, for example by organic material, during the use of the endoscope. To clean the lens surface of the lens element 20, a cleaning nozzle is arranged at the distal housing element 10. The cleaning nozzle is supplied from the proximal side via a medium channel, not shown, with a cleaning medium which is released from the cleaning nozzle. Water, air or another suitable compatible cleaning medium can be used as the cleaning medium. The release of the cleaning medium can be controlled on demand.

The cleaning nozzle has a nozzle element 30, which is arranged at the distal side of the distal housing element 10. The nozzle element 30 is arranged adjacent to and spaced apart from the lens element 20. The nozzle element 30 is arranged at the distal side 12.

The nozzle element 30 has a nozzle opening 31 which is directed toward the lens element 20. The nozzle opening 31 is formed as an elongated medium outlet slit, see FIG. 1. The elongated medium outlet slit extends transverse to the extension direction of the distal housing element 10 and transverse to the extension direction of the endoscope. In other words, the elongated medium outlet slit extends transverse to the central axis of the distal housing element 10. The medium channel extends through the endoscope and opens at the distal side 12 in the nozzle element 30.

The nozzle element 30 has a side wall 32, which is open on the side facing the lens element 20. The side of the side wall 32, which is open toward the lens element 20, forms the nozzle opening 31. The side wall 32 protrudes from the distal side 12 in the distal direction. In other words, the side wall 32 is positioned on the distal side 12 of the distal housing element 10.

At the distal side, the side wall 32 is covered by a nozzle cover 33. The rim of the nozzle cover 33 facing the lens element 20 forms the upper (distal) boundary of the nozzle opening 31. The lateral sides of the nozzle opening 31 are each bounded by a portion of the side wall 32. The lower (proximal) boundary of the nozzle opening 31 is formed by the distal side 12 of the distal housing element 10. The upper (distal) boundary of the nozzle opening 31 is straight. The lower (proximal) boundary of the nozzle opening 31 is curved toward the distal side, i.e. curved inwards—toward the nozzle cover 33. The lower (proximal) boundary of the nozzle opening 31 is thus curved concavely. The concave curvature of the lower boundary of the nozzle opening 31 results from the shape of the distal side 12, which rises in the distal direction from the edge of the distal housing element 10 toward the center.

The nozzle opening 31 thus forms a single distal opening of the nozzle element 30 in the form of a slit. The slit is elongated and extends transverse to the axis of the distal housing element 10. The nozzle opening surface normal of the nozzle opening 31 is directed toward the lens element 20, see the arrow in FIG. 3. When the center of the slit of the nozzle opening 31 and the center of the curved lens element 20 are connected by a straight line, this straight line is perpendicular to the extension surface of the slit of the nozzle opening 31. At the outlet of the nozzle element 30, the nozzle opening 31 is narrow.

Figure 2:
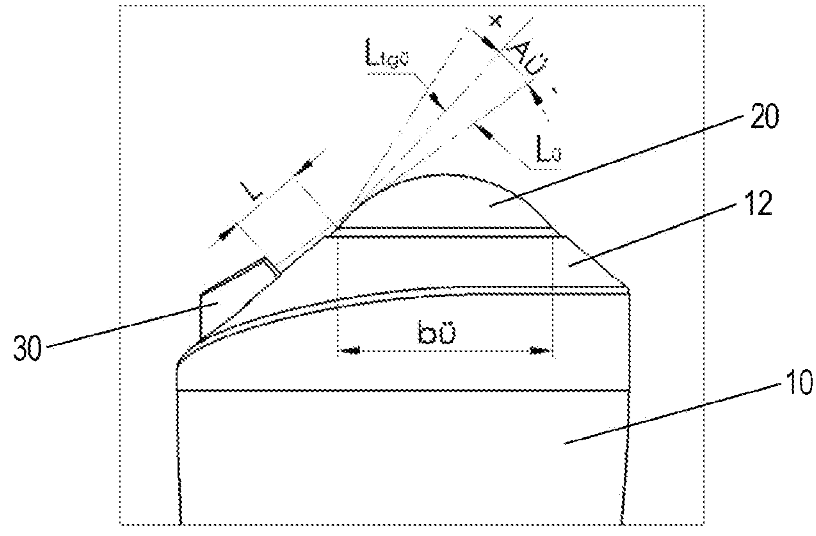
FIG. 2 shows a schematic side view of the distal housing element of the first example.

In this example, the distal nozzle opening 31 is arranged proximal to the proximal edge of the curved lens element 20, see FIG. 2. The proximal edge of the curved lens element 20 refers to the proximal part of the lens element 20, which protrudes in a distal direction from the distal side 12. Thus, when the distal housing element 10 is viewed from the side, the nozzle cover 33, and in particular the rim of the nozzle cover 33 that bounds the nozzle opening 31, is arranged proximal to the proximal edge of the curved lens element 20.

Size Relations in the First Example

For a better understanding of the invention, detailed relations between the nozzle element 30 and the lens element 20 are explained below.

The nozzle element 30 is spaced apart from the lens element 20. In particular, the nozzle opening 31 is at a distance L from the proximal edge of the curved lens element 20. The distance L is measured in the outflow direction Lü of the fluid released from nozzle element 30, i.e. perpendicular to the cross-sectional area of the nozzle opening 31.

The lens element 20 has an area Fu to be flowed over with a width bü, wherein the width bü is measured at the proximal edge of the curved lens element 20.

The inventors of the present invention have deliberated and carried out simulations in order to find an optimized structure with the nozzle element 30 and the lens element 20.

The results of these deliberations and simulations are reflected in the specific size specifications and size relations set out below. More detailed results are shown in the second example.

In the simulations, the effect when releasing a cleaning medium (here water was used) for washing the curved lens element 20 and the effect when releasing air to dry the curved lens element 20 was assumed.

The combination of housing element 10, lens element 20, and nozzle element 30 formed according to the invention showed advantageous results for the release of water even at standard pressures, velocities, and volume flow rates.

The almost hemispherical exposed lens surface of the lens element 20 protrudes in the distal direction from the proximal edge of the lens element 20.

The slit of the nozzle opening 31 has a width bd and a height hd, see FIG. 1. The height hd is measured at the rim of the nozzle opening 31 bounded by the side wall 32. The open area of the nozzle opening 31 is Fd. At the slit of the nozzle opening 31, the width bd has a larger extent than the height hd.

Good results are found when flushing the lens surface of the lens element 20 using the nozzle element 30 if the direction and angle of the flow exiting the nozzle opening 31 are taken into account.

FIG. 2 shows the direction and angle of a flow released from the cleaning nozzle in a side view. Ltgü denotes the tangent to the lens surface of the curved lens element 20 at the proximal edge of the curved lens element 20.

Particularly advantageous flushing results can be achieved if the direction of the outgoing flow Lu relative to the tangent Ltgü at the edge of the surface to be flowed over covers the following angle range: $-10°<Aü<+20°$.

The direction of the outgoing flow Lü is assumed to be the outflow direction of the fluid released from the nozzle element 30 perpendicular to the cross-sectional area of the nozzle opening 31 and passing through the geometric center of the cross-sectional area of the nozzle opening 31, see FIG. 2.

In other words, the flow exiting the distal nozzle opening 31 is directed toward the proximal edge of the curved lens element 20. The direction of the outgoing flow with respect to a tangent Ltgü at the proximal edge of the curved lens element 20 covers an angle of $-10°<Ltgü<+20°$, wherein a positive angle extends away from the curved lens element 20 at the proximal edge of the curved lens element 20 and a negative angle extends into the curved lens element 20 at the proximal edge of the curved lens element 20. The angle of the flow exiting the distal nozzle opening relative to the tangent at the edge of the curved lens element to the lens surface of the curved lens element 20 is determined, among others, by the inclination of the nozzle cover 33 relative to the axis of the distal housing element 10. In other words, it is the inclination of the nozzle cover 33 relative to the distal side 12 of the distal housing element 10. Advantageously, the nozzle cover 33 is inclined by 5° relative to the distal side 12 of the distal housing element 10. It is particularly advantageous if the nozzle cover 33 is inclined by 10° relative to the distal side 12 of the distal housing element 10.

Mode of Operation

If, during use of the endoscope, the user detects that the image quality of the image acquired via the lens element 20 decreases due to a contamination of the lens surface of the curved lens element 20, they will start a cleaning process.

The cleaning nozzle with the nozzle element 30 is supplied with a cleaning medium from the proximal side. The pressurized cleaning medium enters the interior of the nozzle element 30. The interior of the nozzle element 30 is bounded at the sides by the side wall 32 and at the distal side by the nozzle cover 33. Only the elongated, i.e. slit-like, nozzle opening 31 allows the cleaning medium to escape.

Thus, the cleaning medium in the interior of the nozzle element 30 undergoes a reversal of direction toward the lens element 20. Due to the slitted structure of the nozzle opening 31, a flow is released from the nozzle opening 31 that is matched to the shape of the nozzle opening 31, i.e. a wide flow limited in height by the dimension hd.

The distal nozzle opening 31 is arranged spaced apart from the proximal edge of the curved lens element 20 by a distance L. The flow of the cleaning medium released from the nozzle opening 31 increases in width with increasing distance from the nozzle opening 31 in a region after exiting the nozzle opening 31.

Figure 3:
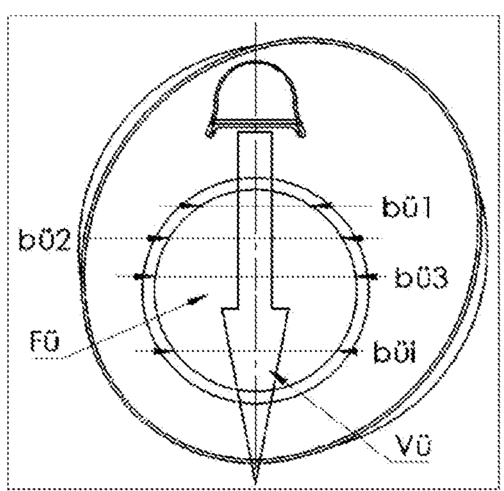
FIG. 3 shows a schematic plan view from the distal side onto the housing element of the first example.

When the flow of the cleaning medium released from the nozzle opening 31 reaches the proximal edge of the lens element 20 facing the nozzle element 30, the flow of the cleaning medium has assumed a width, bü1 in FIG. 3, that encompasses at least the entire proximal edge of the lens element 20. As the flow progresses, the width of the flow expands, reaching a broader range at a first third of the lens element 20 that covers the first third of the lens element 20 with a width bü2 starting from the proximal edge of the lens element 20.

As the flow progresses further, the width of the flow expands still further, so that on reaching the center of the lens element 20 it covers at least the maximum width of the surface be that is to be flowed over.

It turns out that the overflow velocity $\Delta V_{Ü}$ according to FIG. 3 behaves in such a way that the difference in the overflow velocity $\Delta V_{Ü}=V_{ümax}-V_{ümin}$ measured along each width line $b_{ü1}$, $b_{ü2}$, $b_{ü3}$ . . . $b_{üi}$ is at most 20% of the average overflow velocity. Thus, the following applies for the overflow velocity $\Delta V_{Ü}$: $-20\%<\Delta V_{ü}>+20\%$.

Thus, despite its curved shape, the lens element 20, can be flowed on evenly as well as over its entire lens surface, thereby cleaning it.

The lens element 20 could be flowed over with the pressures and velocities for the cleaning medium (such as water) that are typical for endoscopes at deployment sites (e.g. hospital, doctor's office, etc.), by using the surface tension of the liquid. An effective cleaning even of the portion of the lens surface of the lens element 20 facing away from the nozzle element 30 was achieved.

After the contamination has been removed by flowing fluid over the lens surface of the lens element 20, the release of the cleaning medium is stopped.

Air is now blown toward the lens element 20 from the same nozzle element 30 to dry the lens surface of the lens element 20.

The cleaning nozzle with the nozzle element 30 is supplied with air from the proximal side. The pressurized air enters the interior of the nozzle element 30. The interior of the nozzle element 30 has the elongated, i.e. slit-like, nozzle opening 31 as the narrowest point (constriction) and allows the air to escape. Due to the slitted structure of the nozzle opening 31, an airflow is released from the nozzle opening 31 that matches the shape of the nozzle opening 31, i.e. a wide flow that is limited in height by the dimension hd.

The airflow released from the nozzle opening 31 increases in width with increasing distance from the nozzle opening 31 in a region after exiting the nozzle opening 31.

When the tip of the airflow released from the nozzle opening 31 reaches the proximal edge of the lens element 20 facing the nozzle element 30, the airflow has assumed a width, $b_{ü1}$ in FIG. 3, that encompasses at least the entire proximal edge of lens element 20. As the airflow progresses, the width of the airflow expands further so that it reaches a wider region at a first third of the lens element 20, which covers the first third of the lens element 20 with a width $b_{ü2}$ starting from the proximal edge of the lens element 20.

As the airflow progresses further, the width of the airflow expands still further, so that on reaching the center of the lens element 20 it covers at least the maximum width of the surface be that is to be flowed over.

It turns out that the overflow velocity $\Delta V_{Ü}$ according to FIG. 3 behaves in such a way that the difference in the overflow velocity $\Delta V_{Ü}=V_{ümax}-V_{ümin}$ measured along each width line $b_{ü1}$, $b_{ü2}$, $b_{ü3}$ . . . $b_{üi}$ is at most 20% of the average overflow velocity. Thus, the following applies for the overflow velocity $\Delta V_{Ü}$: $-20\%<\Delta V_{ü}>+20\%$.

Thus, despite its curved shape, the lens element 20 can be flowed on evenly as well as over its entire lens surface with air, thereby drying it.

The lens element 20 could be flowed over at high velocity without the airflow lifting away from the lens surface.

An effective drying even of the portion of the lens surface of the lens element 20 facing away from the nozzle element 30 was achieved.

In the second example below, this advantageous overflowing effect is explained in more detail.

SECOND EXAMPLE

A second example of the present invention is described below with reference to FIGS. 4 to 7.

FIGS. 4 to 7 show an advantageous flow behavior in a structure according to the invention.

The present example examines the effect of a specific structure example for a particular structure that resulted in the flow behavior of FIGS. 4 to 7.

This example differs from the first example in that a working channel 40 is provided in the distal housing element 10.

A tube-like or channel-like working channel element 41 is provided in the endoscope in such a way that it extends from the proximal side up to the distal housing element 10 and is open at the distal side of the distal housing element 10. The interior of the working channel element 41 forms the working channel 40 through which instruments can be guided. The opening of the working channel element 41 at the distal side of the distal housing element 10 forms a distal working channel opening.

Alternatively, the working channel element 41 can end proximal to the distal working channel opening and open into a working channel portion formed in the distal housing element 10.

The distal working channel opening of the working channel 40 opens at the distal side of the distal housing element 10 at a location that is adjacent to the curved lens element 20 of the first example.

The nozzle element 30 of the first example is arranged proximal to the curved lens element 20.

The nozzle element 30 is arranged at the distal side of the distal housing element 10 in such a way that the distal nozzle opening 31 is directed toward the center of the lens surface of the curved lens element 20 that protrudes toward the distal side. The distal nozzle opening 31 is spaced apart from the proximal edge of the curved lens element 20 by a distance L.

Specific structure that resulted in the flow behavior of FIGS. 4 to 7

Geometric Specifications

L=3 mm bü=6.4 mm hD=0.46 mm bD=2.7 mm

This endoscope with the structure described above resulted in an advantageous fluid release from the nozzle element 30 for drying the lens element 20. The fluid flow is shown in FIGS. 4 to 7 by means of fluid flow lines. The fluid flow lines indicate the course of the fluid flow from the inside of the nozzle element 30 until it flows over the exposed lens surface of the lens element 20. The direction of the fluid flow lines shows the direction of the fluid flow. As can be seen in FIGS. 4 to 7, the flow velocity in the released jet was distributed relatively evenly in the region of the exposed lens surface of the lens element 20 that is flowed over, as can be seen from the few widely spaced gradient lines along the jet.

Figure 4:
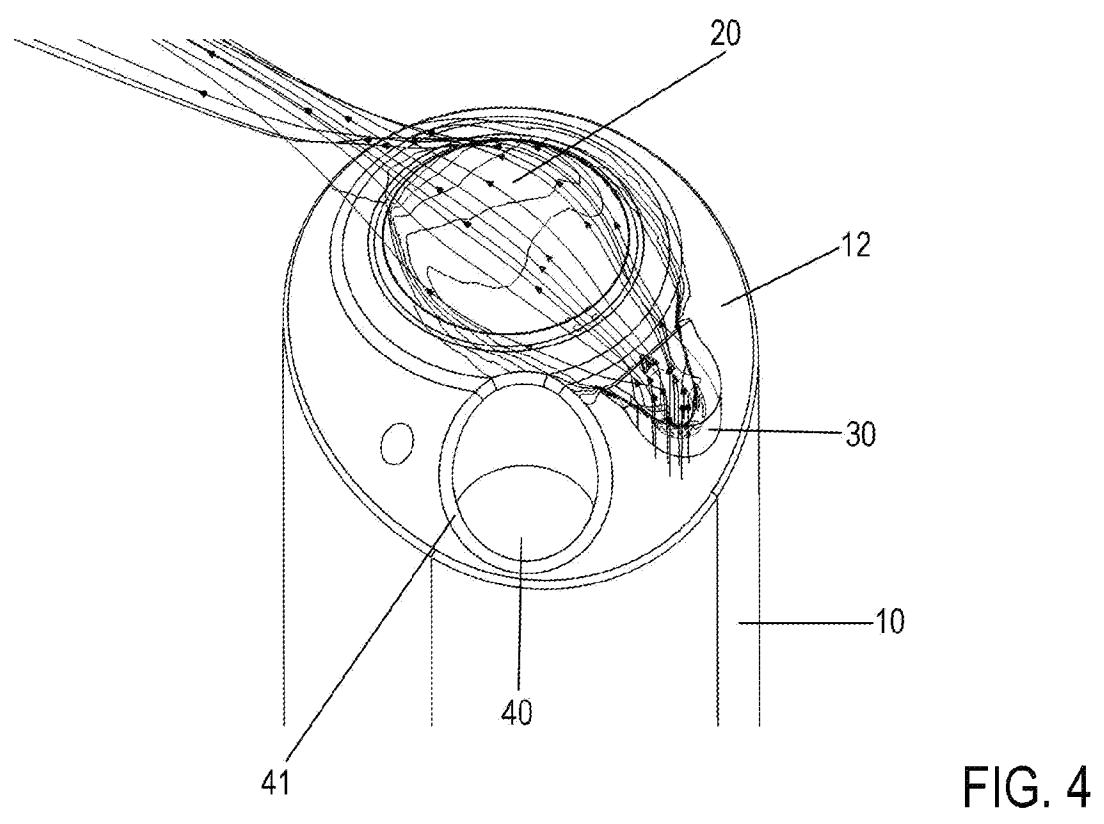
Figure 5:
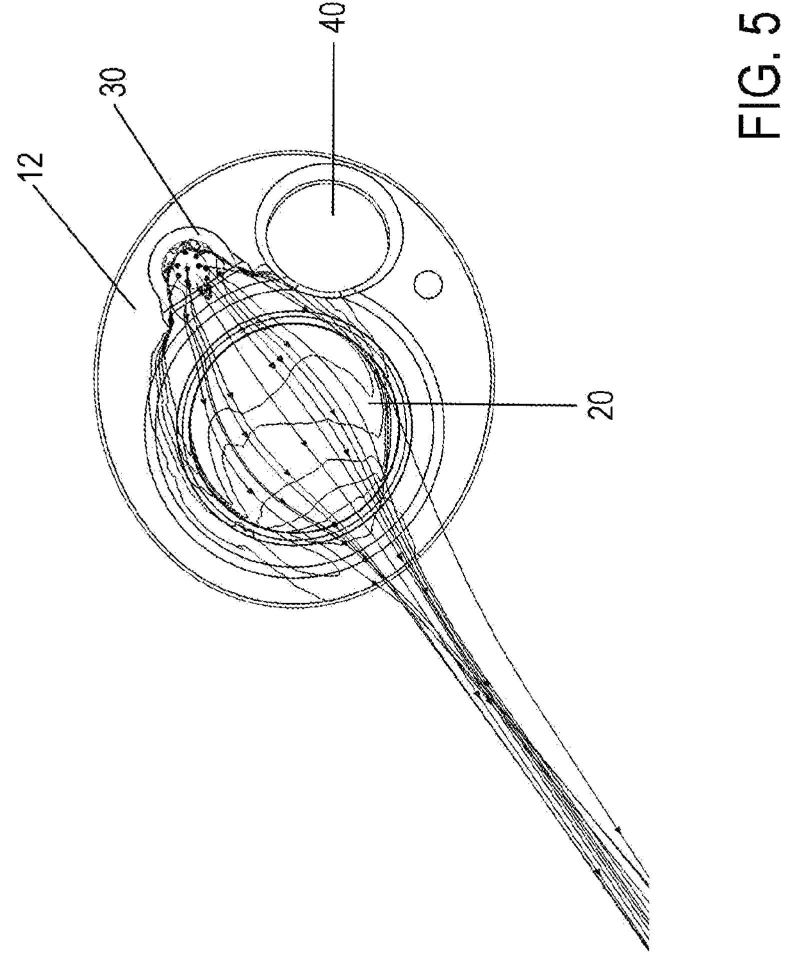
FIG. 5 shows a schematic plan view from the distal side onto the housing element of the second example.
Figure 6:
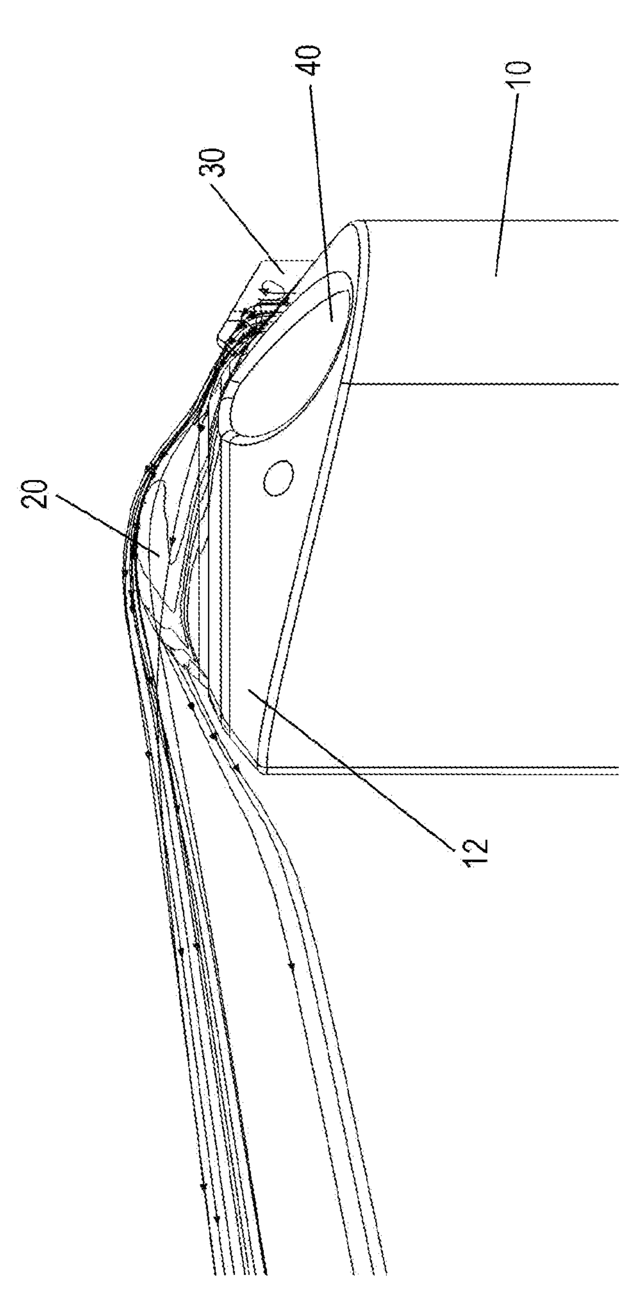
FIG. 6 shows a schematic side view of the distal housing element of the second example.
Figure 7:
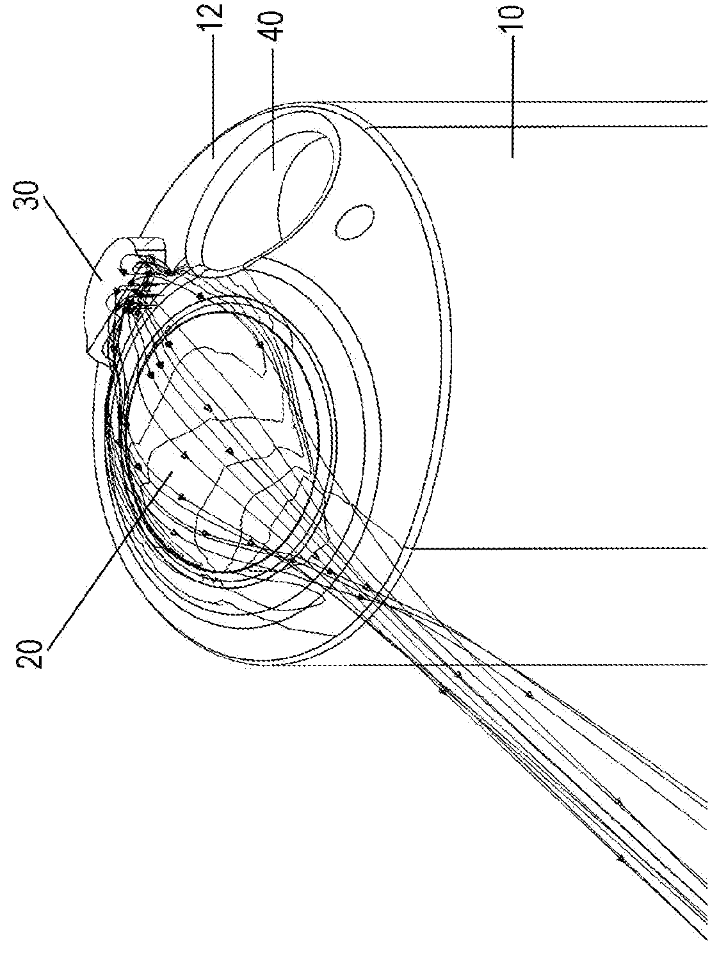
FIG. 7 shows a further schematic plan view from the distal side onto the housing element of the second example.
Figure 8:
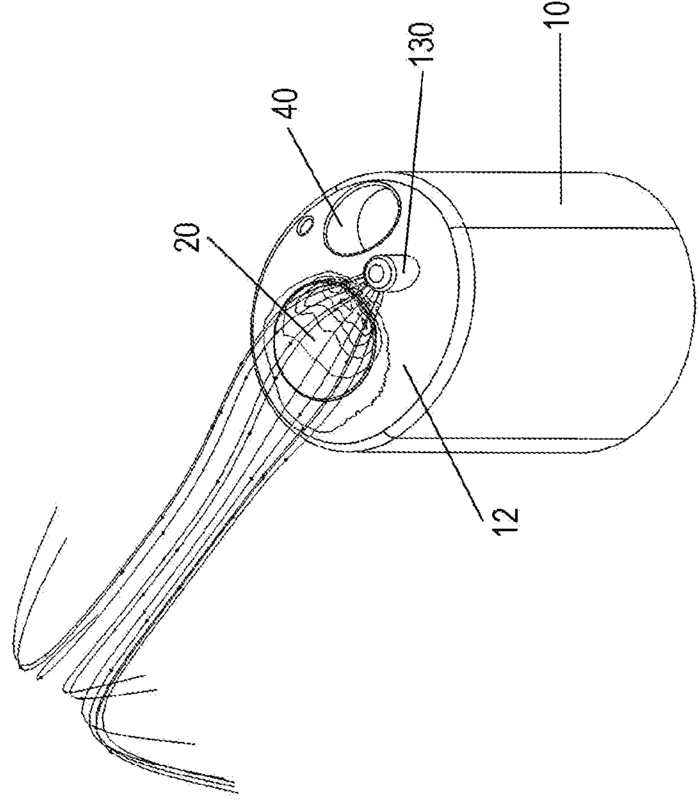
FIG. 8 shows a schematic plan view from the distal side onto a distal housing element with a lens element and a nozzle element in a third example.
Figure 9:
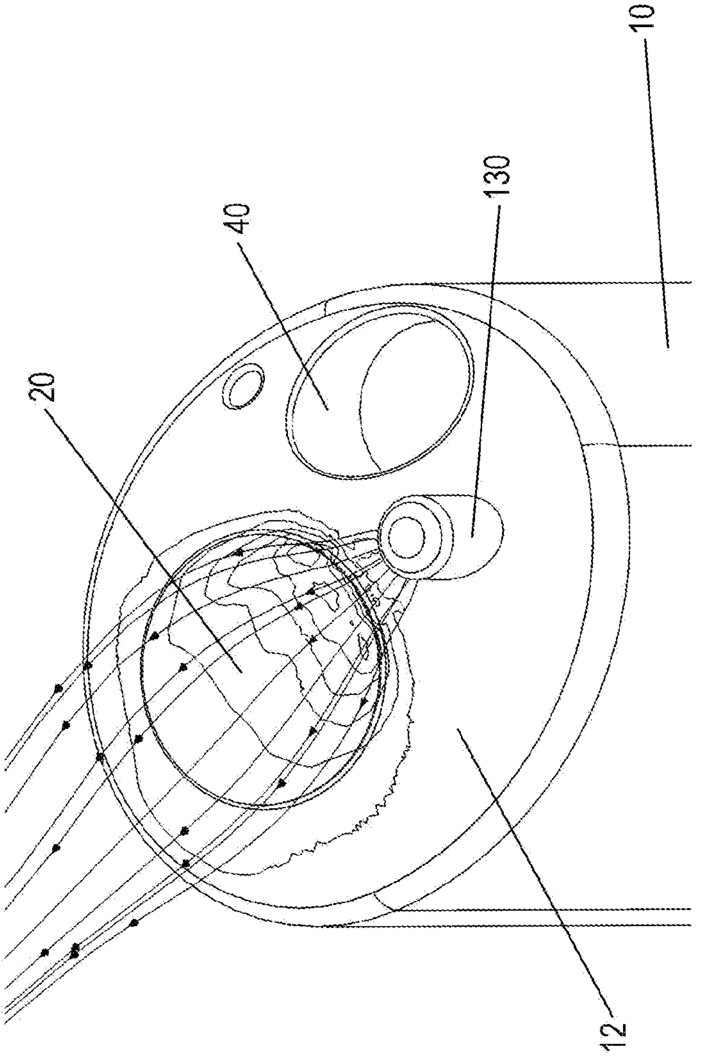
FIG. 9 shows a further schematic plan view from the distal side onto the housing element of the third example.
Figure 10:
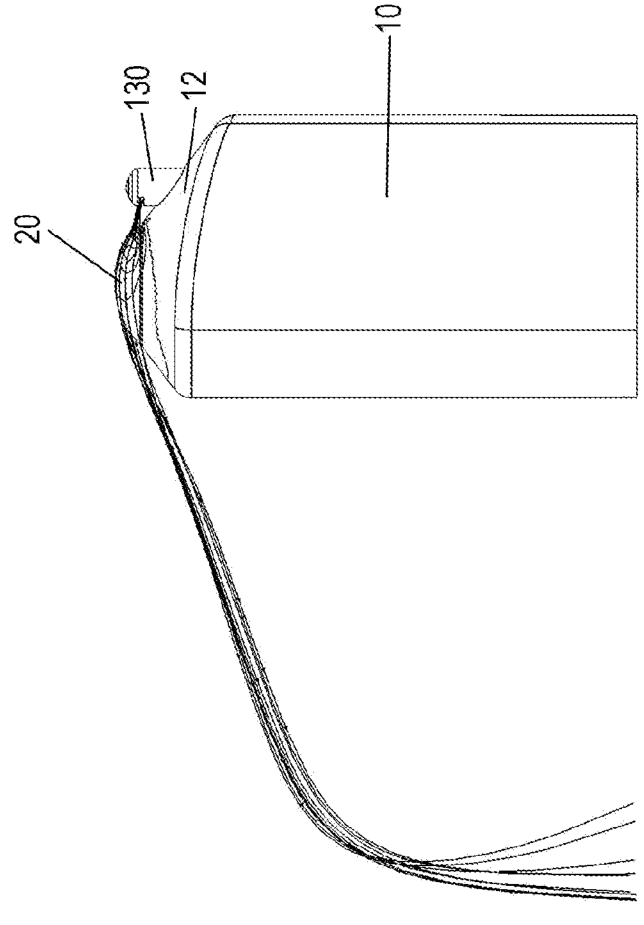
FIG. 10 shows a schematic side view of the distal housing element with the lens element and the nozzle element in the third example.

In particular, the fluid was conveyed to the nozzle element 30 by a pump, not shown. The fluid struck the nozzle cover 33 in the interior of the nozzle element 30. At the nozzle cover 33, the direction of the fluid was changed toward the outlet, i.e. toward the distal nozzle opening 31. Contained by the side walls 32, the nozzle cover 33 and the inclined distal surface on the distal side 12 of the housing element 10, the fluid left the nozzle element 30 through the distal nozzle opening 31 and moved along the inclined distal surface on the distal side 12 of the housing element 10 toward the lens element 20, wherein the fluid flow extended laterally slightly, as shown in FIGS. 4, 5 and 7. Upon arriving at the proximal edge of the lens element 30 facing the nozzle element 30, the fluid flow assumed a lateral extent, which covered the entire proximal edge of the lens element 20 facing the nozzle element 30. The fluid flow then rose at the curved exposed lens surface of the lens element 20 and expanded further laterally and flowed over the entire half of the lens element 20 facing toward the nozzle element 30. After flowing over the center of the exposed lens surface of the lens element 20 which protrudes furthest in the distal direction, the fluid continued to flow, adhering to the exposed lens surface of the lens element 20 due to the laminar flow, see FIG. 6. The fluid reliably flowed over at least the exposed lens surface of the lens element 20 and partly also over the edge portions of the distal side 12 of the housing element 10 abutting the exposed lens surface of the lens element 20.

In FIGS. 4 to 7, in addition to the fluid flow lines, lines of equal velocity of the fluid flow crossing the fluid flow lines are shown. Thus, it can be seen that when arriving at the proximal edge of the lens element 20 facing the nozzle element 30, the fluid had a higher velocity at the edge regions of the fluid flow than at the center of the fluid flow directed toward the center of the exposed lens surface of the lens element 20.

During the simulation of FIGS. 4 to 7, the endoscope was held in such a way that the distal housing element 10 stood upright and the lens element 20 pointed upwards. Further investigations showed that similar results were also seen at all other arrangements of the distal housing element 10 in space. Even with the lens element 20 pointing downwards, the beneficial effects for cleaning the lens element 20 with the cleaning medium and drying with air could be achieved.

Simulations of a general structure of housing element 10, lens element 20 and nozzle element 30, and conclusion from the simulations In the following simulations, it was found under which conditions the optimal overflowing results occur in the first and second examples.

In the following simulations the same conditions were applied to the connection pressure of the supplied air as in the previous example. This means that the endoscope was connected to a pressurized air supply corresponding to a common pressurized air supply present in hospitals/doctor's offices etc. The endoscope used had a medium channel of a typical size with a flow cross-section.

Lens elements 20 in different widths bü (and corresponding areas Fü) were combined with nozzle elements 30 of different nozzle opening areas Fd (width bD and height hD) and tested in simulations to find out which combinations provide advantageous overflowing results.

In the following simulated configurations, particularly advantageous overflowing results of a complete overflowing/drying of the lens element 20 were obtained without breakdown of the flow on the distal side 12 of the housing element 10.

In the following table:

bü=width of the lens element 20 flowed over in mm

Fü=area of the lens element 20 flowed over in mm$^2$ bD=nozzle width in mm hD=nozzle height in mm L=distance in mm from the outlet surface of the nozzle element 30 to the proximal edge of the lens element 20

| $b_ü$ | $F_ü$ | $b_D$ | $h_D$ | L≤ |
|---|---|---|---|---|
| 3.0 | 8 | 1.00 | 0.20 | 1.50 |
| 3.0 | 8 | 1.25 | 0.16 | 1.20 |
| 3.0 | 8 | 1.50 | 0.13 | 0.80 |
| 3.0 | 8 | 1.75 | 0.12 | 0.46 |
| 3.0 | 8 | 2.00 | 0.10 | 0.23 |
| 3.0 | 8 | 2.25 | 0.09 | 0.10 |
| 3.0 | 8 | 2.50 | 0.08 | 0.04 |
| 3.0 | 8 | 2.75 | 0.07 | 0.01 |
| 3.0 | 8 | 2.90 | 0.07 | 0.01 |
| 5.0 | 22 | 1.0 | 0.55 | 2.50 |
| 5.0 | 22 | 1.5 | 0.37 | 1.67 |
| 5.0 | 22 | 2.0 | 0.28 | 1.25 |
| 5.0 | 22 | 2.5 | 0.22 | 1.00 |
| 5.0 | 22 | 3.0 | 0.18 | 0.83 |
| 5.0 | 22 | 3.5 | 0.16 | 0.71 |
| 5.0 | 22 | 4.0 | 0.14 | 0.62 |
| 5.0 | 22 | 4.5 | 0.12 | 0.56 |
| 7.0 | 44 | 1.0 | 1.09 | 3.50 |
| 7.0 | 44 | 1.5 | 0.73 | 2.33 |
| 7.0 | 44 | 2.0 | 0.55 | 1.75 |
| 7.0 | 44 | 2.5 | 0.44 | 1.40 |
| 7.0 | 44 | 3.0 | 0.36 | 1.17 |
| 7.0 | 44 | 3.5 | 0.31 | 1.00 |
| 7.0 | 44 | 4.0 | 0.27 | 0.87 |
| 7.0 | 44 | 4.5 | 0.24 | 0.78 |
| 7.0 | 44 | 5.0 | 0.22 | 0.70 |
| 7.0 | 44 | 5.5 | 0.20 | 0.64 |
| 7.0 | 44 | 6.0 | 0.18 | 0.58 |
| 7.0 | 44 | 6.5 | 0.17 | 0.54 |
| 10.0 | 94 | 1 | 2.34 | 5.00 |
| 10.0 | 94 | 1.5 | 1.56 | 3.33 |
| 10.0 | 94 | 2.0 | 1.17 | 2.50 |
| 10.0 | 94 | 2.5 | 0.94 | 2.00 |
| 10.0 | 94 | 3.0 | 0.78 | 1.67 |
| 10.0 | 94 | 3.5 | 0.67 | 1.43 |
| 10.0 | 94 | 4.0 | 0.59 | 1.25 |
| 10.0 | 94 | 4.5 | 0.52 | 1.11 |
| 10.0 | 94 | 5.0 | 0.47 | 1.00 |
| 10.0 | 94 | 5.5 | 0.43 | 0.91 |
| 10.0 | 94 | 6.0 | 0.39 | 0.83 |
| 10.0 | 94 | 6.5 | 0.36 | 0.77 |
| 10.0 | 94 | 7.0 | 0.33 | 0.71 |
| 10.0 | 94 | 7.5 | 0.31 | 0.67 |
| 10.0 | 94 | 8.0 | 0.29 | 0.62 |
| 10.0 | 94 | 8.5 | 0.28 | 0.59 |
| 10.0 | 94 | 9.0 | 0.26 | 0.56 |
| 10.0 | 94 | 9.5 | 0.25 | 0.53 |
| 12.0 | 130 | 1 | 3.24 | 6.00 |
| 12.0 | 130 | 1.5 | 2.16 | 4.00 |
| 12.0 | 130 | 2.0 | 1.62 | 3.00 |
| 12.0 | 130 | 2.5 | 1.30 | 2.40 |
| 12.0 | 130 | 3.0 | 1.08 | 2.00 |
| 12.0 | 130 | 3.5 | 0.93 | 1.71 |

-continued

| $b_{ü}$ | $F_{ü}$ | $b_D$ | $h_D$ | L≤ |
|---|---|---|---|---|
| 12.0 | 130 | 4.0 | 0.81 | 1.50 |
| 12.0 | 130 | 4.5 | 0.72 | 1.33 |
| 12.0 | 130 | 5.0 | 0.65 | 1.20 |
| 12.0 | 130 | 5.5 | 0.59 | 1.09 |
| 12.0 | 130 | 6.0 | 0.54 | 1.00 |
| 12.0 | 130 | 6.5 | 0.50 | 0.92 |
| 12.0 | 130 | 7.0 | 0.46 | 0.86 |
| 12.0 | 130 | 7.5 | 0.43 | 0.80 |
| 12.0 | 130 | 8.0 | 0.41 | 0.75 |
| 12.0 | 130 | 8.5 | 0.38 | 0.71 |
| 12.0 | 130 | 9.0 | 0.36 | 0.67 |
| 12.0 | 130 | 9.5 | 0.34 | 0.63 |
| 12.0 | 130 | 10.0 | 0.32 | 0.60 |
| 12.0 | 130 | 10.5 | 0.31 | 0.57 |
| 12.0 | 130 | 11.0 | 0.29 | 0.55 |
| 12.0 | 130 | 11.5 | 0.28 | 0.52 |
| 14.0 | 175 | 1 | 4.38 | 7.00 |
| 14.0 | 175 | 1.5 | 2.92 | 4.67 |
| 14.0 | 175 | 2.0 | 2.19 | 3.50 |
| 14.0 | 175 | 2.5 | 1.75 | 2.80 |
| 14.0 | 175 | 3.0 | 1.46 | 2.33 |
| 14.0 | 175 | 3.5 | 1.25 | 2.00 |
| 14.0 | 175 | 4.0 | 1.09 | 1.75 |
| 14.0 | 175 | 4.5 | 0.97 | 1.56 |
| 14.0 | 175 | 5.0 | 0.88 | 1.40 |
| 14.0 | 175 | 5.5 | 0.80 | 1.27 |
| 14.0 | 175 | 6.0 | 0.73 | 1.17 |
| 14.0 | 175 | 6.5 | 0.67 | 1.08 |
| 14.0 | 175 | 7.0 | 0.63 | 1.00 |
| 14.0 | 175 | 7.5 | 0.58 | 0.93 |
| 14.0 | 175 | 8.0 | 0.55 | 0.87 |
| 14.0 | 175 | 8.5 | 0.52 | 0.82 |
| 14.0 | 175 | 9.0 | 0.49 | 0.78 |
| 14.0 | 175 | 9.5 | 0.46 | 0.74 |
| 14.0 | 175 | 10.0 | 0.44 | 0.70 |
| 14.0 | 175 | 10.5 | 0.42 | 0.67 |
| 14.0 | 175 | 11.0 | 0.40 | 0.64 |
| 14.0 | 175 | 11.5 | 0.38 | 0.61 |
| 14.0 | 175 | 12.0 | 0.36 | 0.58 |
| 14.0 | 175 | 12.5 | 0.35 | 0.56 |
| 14.0 | 175 | 13.0 | 0.34 | 0.54 |
| 14.0 | 175 | 13.5 | 0.32 | 0.52 |

For the respective lens elements 20, worse results were obtained with incomplete overflowing when combined with nozzle elements 30 which each had a width bD and height hD above the values of the width bD and height hD listed above.

For example, the overflowing of the lens element 20 was incomplete in the following configurations.

| $b_{ü}$ | $F_{ü}$ | $b_D$ | $h_D$ | L≤ |
|---|---|---|---|---|
| 5.0 | 22 | 1.00 | 0.5 | 4.40 |
| 14.0 | 180 | 1.00 | 0.38 | 4.75 |

Evaluation of the Simulations

Optimal results for a complete overflowing/drying of the lens element 20 without the flow breaking down on the distal side 12 of the distal housing element 10 could be achieved with a design using a geometric structure that satisfied the following conditions:

$$Bü/bD>1 \rightarrow bü>bD \quad (1)$$

$$30<Fü/Fd<40 \quad (2)$$

$$L<0.5*bü \quad (3)$$

$$bD/hD>1 \quad (4)$$

wherein the outlet surface cross-sectional area Fd of the nozzle element 30 was assumed to be approximately bD*hD.

It was also found that the above-mentioned combinations of housing element 10, lens element 20 and nozzle element 30, formed according to the invention, showed advantageous results for the release of water and air at the usual pressures, velocities and volume flow rates.

In summary, it could be concluded that the following conditions were decisive in achieving the desired result of sufficient overflowing of at least the entire exposed lens surface of the lens element 20 with the cleaning medium and for drying with air:

$$bü/bD>1 \rightarrow bü>bD \quad (1)$$

With bü<bD and bü=bD, the overflowing of the exposed lens surface of the lens element 20 with laminar flow was made more difficult. The results deteriorated.

$$30<Fü/FD<40 \quad (2)$$

In other words, the surface that is flowed over must be at least 30× and at most 40× larger than the opening area of the nozzle.

Outside this range, the overflowing of at least the exposed lens surface of the lens element 20 deteriorated.

$$L<0.5*bü \quad (3)$$

L, the distance of the nozzle from the lens edge, is at most ½ times as large as the diameter of the lens bü

At a greater distance L, the overflowing of the exposed lens surface of the lens element 20 deteriorated.

Possible range of dimensioning for lenses used in the endoscope:

$$3\ \text{mm}<bü<14\ \text{mm} \rightarrow L=1.5\ \ldots\ 7\ \text{mm}$$

$$bD/hD>1 \quad (4)$$

i.e. bD (nozzle opening width) is always greater than hD (nozzle opening height)

AND

The nozzle width must be smaller than the width that is flowed over, see (1).

The nozzle cross-section can be almost square if the nozzle opening height $h_D$ is slightly smaller than the nozzle opening width bD, see (4)

A degraded but still acceptable overflowing result was found with bD=hD.

With hD greater than bD, the overflowing of the exposed lens surface of the lens element 20 deteriorated.

Deviations of 10% of the above values could be tolerated without the result deteriorating fundamentally.

In addition, the simulations revealed that employed lens elements with an overflow width of 5.0 mm<bü<9.0 mm showed particularly good results.

The examples with 5.0 mm>bü resulted in too low a light intensity and bü>9.0 mm resulted in too large a structure on the distal housing element 10.

Thus, lens elements with 5.0 mm>bü resulted in a less suitable field of view, and lens elements with bü>9.0 mm resulted in an unfavorable lens diameter in relation to the endoscope diameter.

Furthermore, it was recognized that a complete overflowing could not be ensured for 1.0 mm>L and that the resulting structure was too large for L>3.0 mm.

A further example is described below in order to better understand the structure, the effect and the advantages of the invention.

THIRD EXAMPLE

The third example uses a different nozzle element 130 instead of the nozzle element 30 of the first and second examples. The remaining structure is the same as in the second example.

The nozzle element 130 is arranged at the distal side 12 of the distal housing element 10. The nozzle element 130 is arranged adjacent to and spaced apart from the lens element 20. The nozzle element 130 has a cylindrical cross-section and extends tubular from the distal side 12 of the distal housing element 10.

The nozzle element 130 has a nozzle opening 133 which is directed toward the lens element 20. The nozzle opening 133 is formed as an elongated medium outlet slit, see FIG. 11. The elongated medium outlet slit extends transverse to the extension direction of the distal housing element 10 and transverse to the extension direction of the endoscope. In other words, the elongated medium outlet slit extends transverse to the central axis of the distal housing element 10.

At the distal side, the tubular nozzle element 130 has a nozzle cover 132 that closes the distal side of the tubular nozzle element 130. At the distal side, the nozzle cover 132 is curved toward the distal side in order to facilitate the insertion of the endoscope in the distal direction. Proximal from the nozzle cover 132, the nozzle opening 133 is formed at the outer circumference of the nozzle element 130.

The lateral sides of the nozzle opening 133 are each formed by a portion of the tubular nozzle element 130. The lower (proximal) boundary of the nozzle opening 133 is formed by the distal side 12 of the tubular nozzle element 130. The upper (distal) boundary of the nozzle opening 133 is formed by a proximal side of the nozzle cover 132. At the outlet of the nozzle element 30, the nozzle opening 133 is thus flat.

The nozzle opening 133 thus forms a single distal opening of the nozzle element 130 in the form of a slit. The slit is elongated and extends transverse to the axis of the distal housing element 10. The slit of the nozzle opening 133 is directed toward the center of the lens element 20. When the center of the slit of the nozzle opening 133 and the center of the curved lens element 20 are connected by a straight line, this straight line is perpendicular to the extension surface of the slit of the nozzle opening 133.

Figure 11:
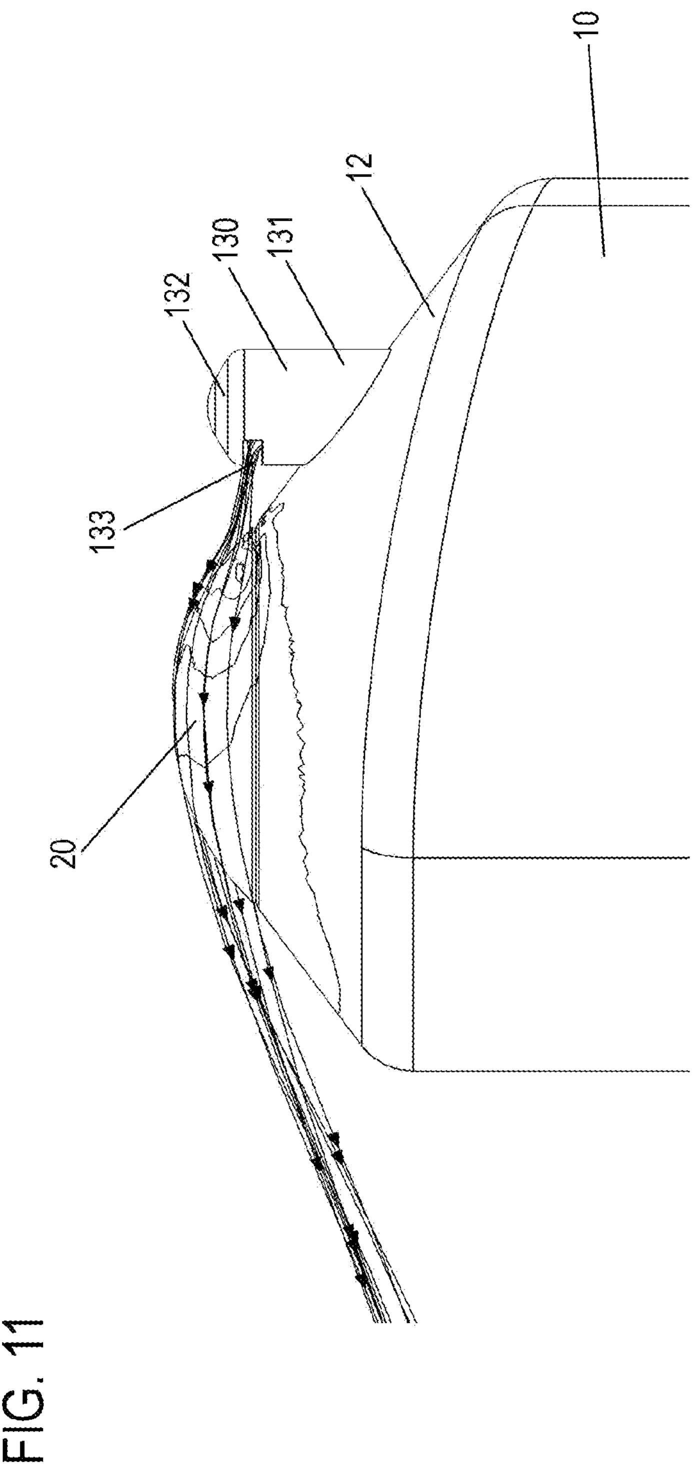
FIG. 11 shows a further schematic side view of the distal housing element of the third example.
Figure 12:
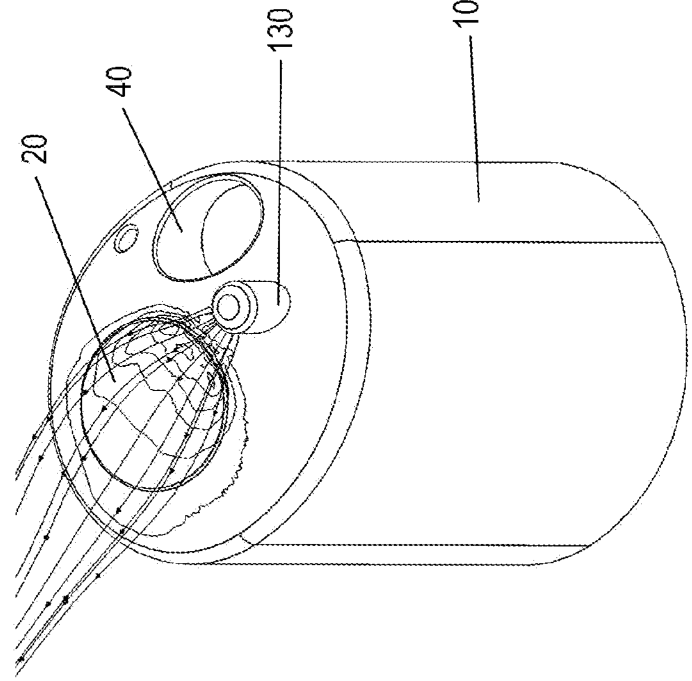
FIG. 12 shows a further schematic perspective view of the distal housing element of the third example.

In this example, the distal nozzle opening 133 is arranged opposite the proximal edge of the curved lens element 20, see FIG. 11.

The flow behavior of the fluid released from the nozzle element 130 was only slightly worse than in the previous example.

The flow velocity in the released jet was less uniformly distributed in the region of the exposed lens surface of the lens element 20 that is flowed over compared to the previous example, as can be seen from the many narrowly spaced gradient lines along the jet.

Thus, a structure of the third example can be applied in an endoscope, but the structure of the first and second examples is preferred.

FOURTH EXAMPLE

Figure 13:
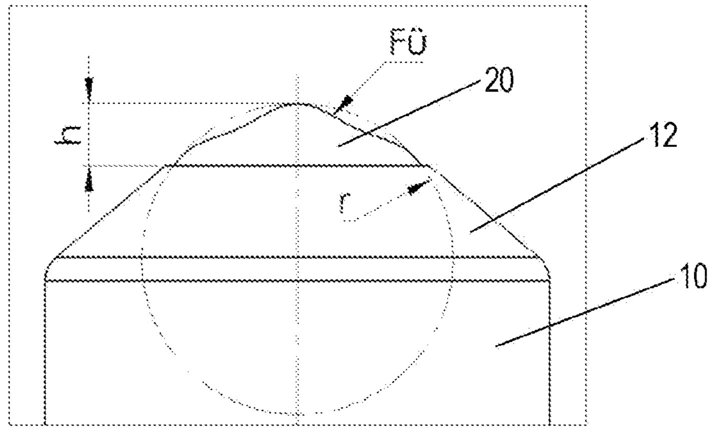
FIG. 13 shows a schematic side view of a distal housing element in a fourth example.

FIG. 13 shows a schematic side view of a distal housing element in a fourth example.

In the first to third examples, the lens element 20 is a curved lens element with spherical curvature.

In this example, the lens element 20 is a curved lens element with aspherical curvature. The lens element 20 has a radius r at the center of the exposed lens surface facing toward the distal side, see FIG. 13. The center of the exposed lens surface facing toward the distal side protrudes from the proximal edge of the exposed lens surface by the height h in the distal direction.

On the proximal side of the center of the exposed lens surface, the radius of the lens element 20 decreases such that a concavity is formed. The concavity of the lens element 20 lies between the distal center of the exposed lens surface and the proximal edge of the exposed lens surface.

This aspherical lens element 20 can also be combined advantageously with the nozzle according to the invention from the first to third examples.

Alternatives

The almost hemispherical exposed lens surface of the lens element 20 in the examples described can have a height of approximately 2 mm in the distal direction from the proximal edge of the lens element 20. The lens element 20 in the examples described can have a surface area of the exposed lens surface of more than 40 $mm^2$.

In the examples, the lens element 20 is arranged spaced apart from the circumferential edge of the distal housing element 10. The invention is not limited to this. The lens element 20 can also be arranged at the circumferential edge of the distal housing element 10. When viewed from the distal side, the lens element 20 can thus be arranged eccentrically at the distal side 12.

The distal housing element 10 can also be formed in other shapes apart from a cylinder of circular cross-section or an oval cylinder. When inserting the endoscope, it should only be taken into account that the distal housing element 10 does not form an obstacle or cause interference.

In the examples, the side walls of the nozzle element 30 can be designed in such a way that they approach each other toward the distal nozzle opening 31. This allows a structure to be created in which the cross-sectional area at the distal nozzle opening 31 forms the smallest cross-sectional area in the nozzle element 30.

In an even more advantageous alternative, the cross-sectional area at the distal nozzle opening 31 is the smallest cross-sectional area in the entire fluid supply system formed by the nozzle element 30 and the medium channel leading to the nozzle element 30. As a result, the flow velocity of the medium at the distal nozzle opening 31, which forms the outlet opening of the nozzle element 30, will be largest.

The side walls of the nozzle element 30 can be designed in such a way that they approach each other toward the distal nozzle opening 31 uniformly.

The endoscope can be a rigid or a flexible endoscope.

Further combinations of the examples are possible.

The invention can be advantageously used in any endoscope that uses illumination and acquires images. The invention can be used to clean any type of nozzle.

LIST OF REFERENCE SIGNS

10 distal housing element
12 distal side of the housing element
20 lens element
30 nozzle element
31 distal nozzle opening
32 side wall
33 nozzle cover
40 working channel
41 working channel element
bd width of the distal nozzle opening
bü width of the curved lens element hd height of the distal nozzle opening
Fd nozzle opening area
Fe cross-sectional area of the endoscope at the distal housing element
Fü surface of the lens element to be flowed over
L distance of the distal nozzle opening from the proximal edge of the curved lens element
Lü direction of the outgoing flow
Ltgü tangent at the proximal edge of the curved lens element.

The invention claimed is:

1. An endoscope comprising
a distal housing element having a lens element, and
a nozzle element for cleaning the surface of the lens element;
wherein
the lens element has a convex distalmost lens surface which protrudes from the housing element in a distal direction,
the nozzle element is arranged at a distal side of the distal housing element adjacent to the lens element,
the nozzle element has a distal nozzle opening in the form of an elongated medium outlet slit, directed toward the lens element such that a flow exiting from the nozzle element flows over a side of the distalmost lens surface facing away from the nozzle element,
the distalmost lens surface extends distally beyond the nozzle element, and
the nozzle element is inclined such that the flow exits toward the distal direction.

2. The endoscope according to claim 1, wherein
the elongated medium outlet slit extends transverse to an extension direction of the endoscope.

3. The endoscope according to claim 1, wherein
the lens element has an area (Fü) to be flowed over, which is formed at least by an entire exposed lens surface,
the distal nozzle opening has a nozzle opening area (Fd), wherein 30<Fü/Fd<40.

4. The endoscope according to claim 1, wherein
the distal nozzle opening has a width which is smaller than a width of the lens element at a proximal edge of the lens element.

5. The endoscope according to claim 1, wherein
the distal nozzle opening is aligned with respect to the lens element such that a flow exiting from the distal nozzle opening is directed tangential ±10° with respect to a proximal edge of the lens element.

6. The endoscope according to claim 5, wherein
the flow exiting from the distal nozzle opening is directed with respect to the proximal edge of the lens element at an angle of −10°<Ltgü<+20°, wherein
Ltgü is the tangent to the lens surface of the lens element at the proximal edge of the lens element,
a positive angle extends away from the lens element at the proximal edge of the lens element, and
a negative angle extends into the lens element at the proximal edge of the lens element.

7. The endoscope according to claim 1, wherein
the distal nozzle opening is arranged proximal to a proximal edge of the lens element.

8. The endoscope according to claim 1, wherein
the distal nozzle opening is arranged spaced apart from a proximal edge of the lens element by a distance,
the distance is less than or equal to half a width of the lens element at the proximal edge of the lens element.

9. The endoscope according to claim 1, wherein
a curvature of the lens element is spherical or aspherical.

10. The endoscope according to claim 1, wherein
the distal nozzle opening forms a single distal opening of the nozzle element.

11. The endoscope according to claim 1, wherein
the lens element comprises an area to be flowed over, which is formed by an entire exposed distalmost lens surface, and
the area to be flowed over is greater than a quarter of a cross-sectional area of the endoscope at the distal housing element.

12. The endoscope according to claim 1, wherein
the elongated medium outlet slit, has a width (bd) and a height (hd), wherein hd<bd.

13. The endoscope according to claim 1, wherein
the elongated medium outlet slit has a width (bd) and a height (hd), wherein hd<1 mm<bd.

14. The endoscope according to claim 1, wherein the flow exiting from the nozzle element flows over the side of the distalmost lens surface facing away from the nozzle element due to surface tension.

15. The endoscope according to claim 1, wherein the lens element has a spherical curvature and is one of a fish-eye lens or a wide-angle lens.

16. The endoscope according to claim 1, wherein an overflow velocity $\Delta V_{Ü}$ of the flow exiting from the nozzle element behaves in such a way that the difference in the overflow velocity $\Delta V_{Ü}=V_{ümax}-V_{ümin}$ is at most 20% of an average overflow velocity.

17. The endoscope according to claim 1, wherein:
the nozzle element has a side wall which is open on a side facing the lens element,
the side wall is covered by a nozzle cover,
a rim of the nozzle cover facing the lens element forms a straight distal boundary of the nozzle opening,
lateral sides of the nozzle opening are each bounded by a portion of the side wall,
a proximal boundary of the nozzle opening is formed by the distal side of the distal housing element, and
the proximal boundary of the nozzle opening is concavely curved toward the distal side.

* * * * *